United States Patent
Daum et al.

(10) Patent No.: US 6,865,424 B2
(45) Date of Patent: Mar. 8, 2005

(54) IMPLANTABLE MEDICAL DEVICE WITH VOICE RESPONDING AND RECORDING CAPACITY

(75) Inventors: Douglas R. Daum, Lauderdale, MN (US); Qingsheng Zhu, Little Canada, MN (US); Bruce H. KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 7 days.

(21) Appl. No.: 10/215,237

(22) Filed: Aug. 8, 2002

(65) Prior Publication Data

US 2002/0193847 A1 Dec. 19, 2002

Related U.S. Application Data

(63) Continuation of application No. 09/473,466, filed on Dec. 28, 1999, now Pat. No. 6,453,201, which is a continuation-in-part of application No. 09/421,746, filed on Oct. 20, 1999, now abandoned.

(51) Int. Cl.[7] .............................................. A61N 1/362
(52) U.S. Cl. ........................................ 607/62; 600/586
(58) Field of Search ................................ 600/509, 515, 600/518, 520, 522, 523, 528, 586; 607/2, 4, 9, 17–26, 30, 32, 48–49, 60, 62

(56) References Cited

U.S. PATENT DOCUMENTS

| | | | |
|---|---|---|---|
| 3,586,261 A | 6/1971 | Palme ........................... | 244/1 |
| 3,623,486 A | 11/1971 | Berkovits ................ | 128/419 P |
| 3,631,860 A | 1/1972 | Lopin ....................... | 128/419 P |
| 3,738,369 A | 6/1973 | Adams et al. ........... | 128/419 P |
| 4,066,086 A | 1/1978 | Alferness et al. ........... | 128/421 |
| 4,628,939 A | 12/1986 | Little et al. .................. | 128/696 |
| 4,651,740 A | 3/1987 | Schroeppel ............. | 128/419 P |

(List continued on next page.)

FOREIGN PATENT DOCUMENTS

| | | | |
|---|---|---|---|
| EP | 0491649 | 6/1992 | ............. A61N/1/39 |
| EP | 0558353 | 9/1993 | ............. A61N/1/39 |
| WO | WO-97/43003 | 5/1996 | .......... A61N/1/372 |

OTHER PUBLICATIONS

"Dream Hearing Aid Wish List", http://xp7.dejanews.com/getdoc.xp?recnu . . . db96q2&CONTEXT=862839689.31231&hitnum=0, Published by Deja News, Inc.,(1995),pp. 1–2.

"Future Medical Reports Strong First Quarter Results", http://www.growth.com/DMW/BISdmw.960517.html, Published by Berkshire Information Services, Inc.,(May 17, 1996),pp. 1–3.

"Future Medical Technologies International Announces Launch of New Products", http://www.growth.com/MENU/CVGR/PR/CVGR.950928.html, Published by Future Medical Technologies International,(May 5, 1997),1 page.

(List continued on next page.)

Primary Examiner—Kennedy Schaetzle
Assistant Examiner—Kristen Droesch
(74) Attorney, Agent, or Firm—Schwegman, Lundberg, Woessner & Kluth, P.A.

(57) ABSTRACT

An implantable medical device such as a cardiac pacemaker or implantable cardioverter/defibrillator with the capability of receiving communications in the form of speech spoken by the patient. An acoustic transducer is incorporated within the device which along with associated filtering circuitry enables the voice communication to be used to affect the operation of the device or recorded for later playback.

20 Claims, 1 Drawing Sheet

U.S. PATENT DOCUMENTS

| | | | | |
|---|---|---|---|---|
| 4,725,956 | A | | 2/1988 | Jenkins .................... 364/434 |
| 4,800,883 | A | | 1/1989 | Winstrom ............... 128/419 D |
| 4,850,357 | A | | 7/1989 | Bach, Jr. ................ 128/419 D |
| 4,998,531 | A | | 3/1991 | Bocchi et al. .......... 128/419 D |
| 5,040,212 | A | | 8/1991 | Bethards ..................... 381/41 |
| 5,111,816 | A | | 5/1992 | Pless et al. ........... 128/419 PG |
| 5,129,392 | A | | 7/1992 | Bardy et al. ........... 128/419 D |
| 5,205,285 | A | | 4/1993 | Baker ....................... 128/423 |
| 5,215,083 | A | | 6/1993 | Drane et al. ............ 128/419 D |
| 5,247,945 | A | | 9/1993 | Heinze et al. .............. 607/129 |
| 5,279,293 | A | | 1/1994 | Andersen et al. ............... 607/5 |
| H1347 | H | | 8/1994 | Greeninger et al. .......... 607/30 |
| 5,335,313 | A | | 8/1994 | Douglas .................... 395/2.84 |
| 5,450,525 | A | | 9/1995 | Russell et al. ............. 395/2.84 |
| 5,518,001 | A | | 5/1996 | Snell ........................... 128/697 |
| 5,529,578 | A | | 6/1996 | Struble ........................ 607/29 |
| 5,544,654 | A | | 8/1996 | Murphy et al. .......... 128/660.7 |
| 5,544,661 | A | | 8/1996 | Davis et al. ................. 128/700 |
| 5,594,638 | A | | 1/1997 | Iliff ............................ 395/203 |
| 5,615,380 | A | | 3/1997 | Hyatt ......................... 395/800 |
| 5,633,910 | A | | 5/1997 | Cohen .......................... 379/38 |
| 5,749,908 | A | | 5/1998 | Snell ........................... 607/30 |
| 5,752,976 | A | | 5/1998 | Duffin et al. ................. 607/32 |
| 5,774,357 | A | | 6/1998 | Hoffberg et al. ............ 364/188 |
| 5,792,204 | A | * | 8/1998 | Snell ........................... 607/32 |
| 5,792,205 | A | | 8/1998 | Alt et al. ...................... 607/32 |
| 5,825,283 | A | | 10/1998 | Camhi ........................ 340/438 |
| 5,836,987 | A | * | 11/1998 | Baumann et al. ............. 607/17 |
| 5,843,142 | A | * | 12/1998 | Sultan .......................... 607/49 |
| 5,867,386 | A | | 2/1999 | Hoffberg et al. ............ 364/188 |
| 5,875,108 | A | | 2/1999 | Hoffberg et al. ............ 364/146 |
| 5,888,187 | A | | 3/1999 | Jaeger et al. .................. 600/23 |
| 5,891,180 | A | | 4/1999 | Greeninger et al. .......... 607/32 |
| 5,901,246 | A | | 5/1999 | Hoffberg et al. ............ 382/209 |
| 5,903,454 | A | | 5/1999 | Hoffberg et al. ............ 364/188 |
| 5,920,477 | A | | 7/1999 | Hoffberg et al. ............ 364/148 |
| 5,921,938 | A | * | 7/1999 | Aoyama et al. ............. 600/509 |
| 5,974,340 | A | | 10/1999 | Kadhiresan ................... 607/18 |
| 5,987,352 | A | * | 11/1999 | Klein et al. ................. 600/509 |
| 6,006,132 | A | | 12/1999 | Tacker, Jr. et al. ............... 607/5 |
| 6,453,201 | B1 | * | 9/2002 | Daum et al. .................... 607/62 |

OTHER PUBLICATIONS

"Kurzweil AI and Link Announces Availability of Kurzweil Clinical Reporter for Invasive Cardiology with Datalink", http://www.kurzweil.com/press/971703_card.html, Published by Kurzweil Applied Intelligence, Inc.,(1996)pp. 1–4.

"Kurzweil Clinical Reporter", http://www.kurzweil.com/medical/kcr/faq.html, Published by Kurzweil Applied Intelligence, Inc.,(1996),pp. 1–8.

"Voice Recognition Software in a Medical Office", http://www.voicerecognition.com/medical_office.html, Published by 21st Century Eloquence, Inc.,(May 5, 1997),pp. 1–5.

* cited by examiner

IMPLANTABLE MEDICAL DEVICE WITH VOICE RESPONDING AND RECORDING CAPACITY

CROSS-REFERENCE TO RELATED APPLICATIONS

This application is a continuation of U.S. patent application Ser. No. 09/473,466, filed on Dec. 28, 1999 U.S. Pat. No. 6,453,201, which is a continuation-in-part of U.S. patent application Ser. No. 09/421,746, filed on Oct. 20, 1999 abandoned, which is incorporated herein by reference.

FIELD OF THE INVENTION

This invention pertains to implantable medical devices and to methods and systems for operating same. In particular, the invention relates to means for communicating with such devices.

BACKGROUND

Modem pacemakers typically have the capability to communicate data via a radio-frequency link with an external programming device. Such data is transmitted to the pacemaker in order to program its mode of operation as well as define other operating parameters. Data transmitted from the pacemaker can be used to verify the operating parameters as well as relay information regarding the condition of both the pacemaker and the patient. Pacemaker patients are monitored at regular intervals as part of routine patient care and to check the condition of the device. Among the data which may typically be telemetered from the pacemaker are its programming parameters and an electrogram representing the electrical activity of the heart as sensed by the pacemaker. Pacemakers have also been developed which monitor certain parameters over time while the device is functioning in the patient. Data representing these parameters can be stored in memory for later retrieval using an external programmer.

SUMMARY OF THE INVENTION

It would be desirable in certain situations to be able to communicate with an implantable medical device such as a pacemaker without the need for an external programming device or any kind of equipment such as a radio transmitter/receiver. This would enable a patient, for example, to alter the operation of the device by such communication at any time or place as the need arises. Furthermore, the data recording capabilities of the implantable medical device could be activated by the patient whenever subjective symptoms are noted. The recorded data could then be retrieved later and analyzed for correlation with the symptoms experienced by the patient.

Accordingly, in one embodiment, the present invention is an implantable medical device, such as a cardiac pacemaker or implantable cardioverter/defibrillator, having incorporated therein a system enabling voice communication with the device so that the device responds to voice commands. The system includes an acoustic transducer and processing circuitry for sensing a patient's voice and deriving messages from words spoken by the patient, which messages may then alter the operation of the device. When a patient in whom the device is implanted speaks, the vibrating chords of the larynx cause acoustical energy to be radiated into the thorax where the acoustic transducer converts the energy into electrical audio signals. The audio signals can be analyzed with speech recognition circuitry to recognize certain words that correspond to system messages which are then employed to affect the operation of the device. In certain embodiments of the device, the patient's spoken commands can be used to alter the operating mode of a pacemaker, change operating parameters, or initiate recording of physiological data for later retrieval. Such recorded data can include, for example, electrograms, recordings of the patient's voice, heart sounds, respiratory patterns, or indications of physical activity.

In another embodiment, the invention is an implantable medical device, such as a cardiac pacemaker or implantable cardioverter/defibrillator, having incorporated therein a system enabling voice recording by the device, with the voice recording activated by either an external or internal signal. In the case of externally activated voice recording, the external signal may be, e.g., a voice, tactile, or magnetic signal imparted to the device by the patient or physician. An internal signal may be generated by the device upon sensing a particular physiological condition via its sensing channels, where the particular condition would typically be defined as one where it would be useful to have the subjective impressions of the patient while the condition is present, such as during an arrhythmic episode.

DESCRIPTION OF THE INVENTION

Figure 1:
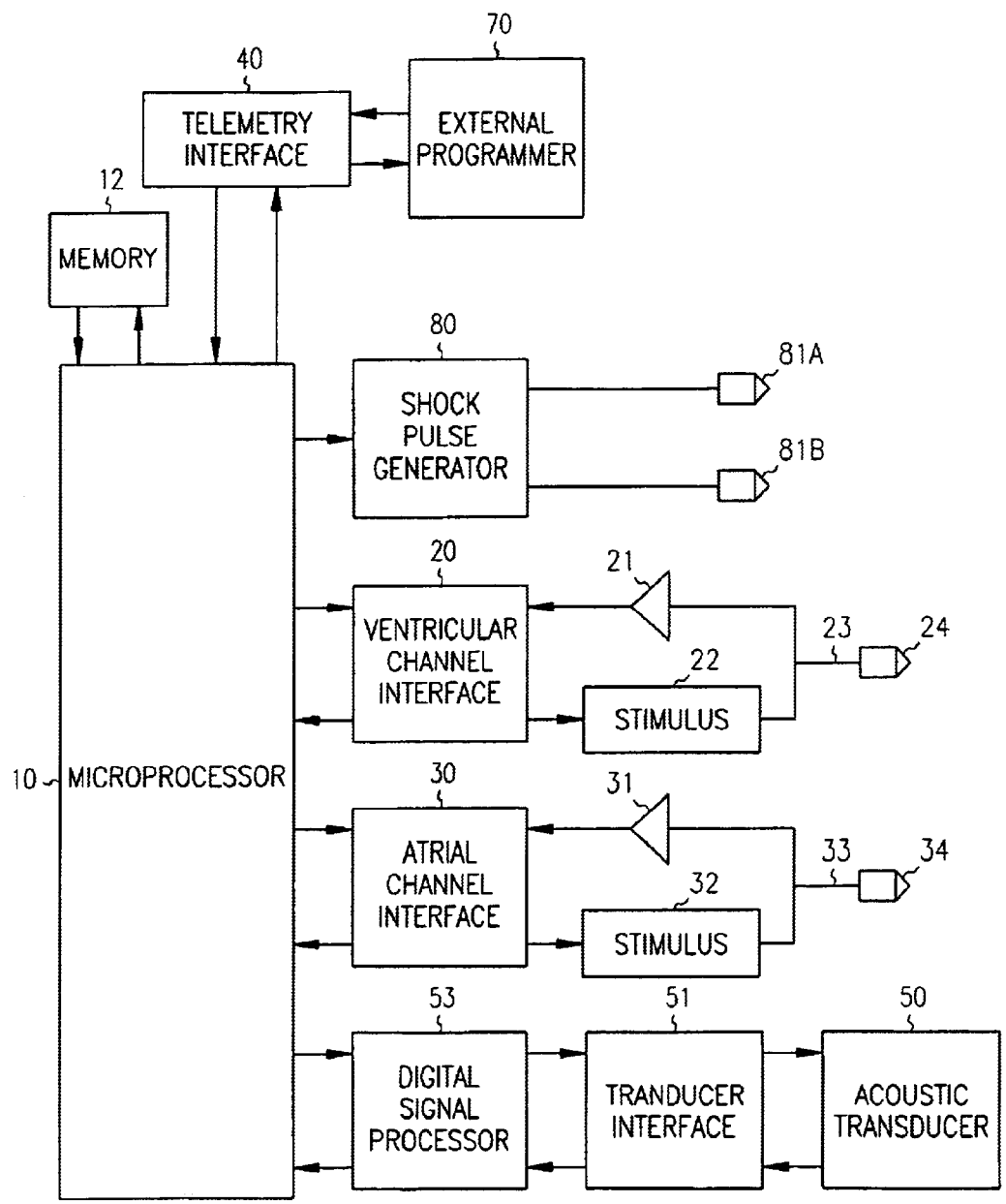
FIG. 1 is a system diagram of an implantable medical device incorporating the invention.

This application hereby incorporates by reference U.S. patent application Ser. No. 09/306,605, filed on May 6, 1999, in its entirety.

In the description that follows, a microprocessor-based pacemaker will be referred to as incorporating the present invention. It should be appreciated, however, the invention could also be incorporated into a pacemaker controlled by custom logic circuitry either in addition to or instead of a programmed microprocessor. The term "circuitry" as used herein should therefore be taken to mean either custom circuitry or a microprocessor executing programmed instructions contained in a processor-readable storage medium along with associated circuit elements.

FIG. 1 shows a system diagram of an implantable medical device, in this case is a microprocessor-based pacemaker with defibrillation and/or antitachycardia pacing capability, that incorporates the present invention. A microprocessor 10 communicates with a system memory 12 via a bidirectional system bus. Memory 12 may typically comprise a ROM for program storage and a RAM for data storage. The overall operation of the device is controlled by a system program running from the memory 12. The microprocessor also has a port for communicating with the telemetry interface 40 which in turn receives programming data from and transmits telemetry data to an external programmer 70 by a radio link.

The pacemaker has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The channel interface includes sampling circuitry and an analog-to-digital converter for digitizing sensing signal outputs from the sensing amplifiers and registers which can be written to by the microprocessor in order to control pacing. A shock pulse generator 80 can also be interfaced to the microprocessor for delivering cardioversion or defibrillation pulses to the heart via a separate pair of electrodes 81a and 81b. Power for the device is provided by a battery.

An acoustic transducer 50 communicates with the microprocessor via a transducer interface 51. The transducer 50 may be an accelerometer or other piezo-resistive device capable of transducing acoustical energy from the patient's body into electrical signals. When the implantable medical device is implanted into a patient, the transducer 50 is capable of producing audio signals corresponding to the patient's voice, as acoustical energy produced by the patient's larynx is radiated into the thorax as well as into the air. The transducer interface 51 includes sampling circuitry for sampling the acoustic transducer output, an analog-to-digital converter for digitizing the samples, and circuitry for interfacing to a digital signal processor 53. Filtering of the transducer signals may also be performed by analog filters in the transducer interface 51 prior to digitization to reduce aliasing effects.

The digital signal processor interfaces to the microprocessor via the system bus and may incorporate speech recognition circuitry for extracting speech information from the digitized transducer signals. Such speech information may constitute specific groups of words that can be decoded into messages recognized by the system program. When such words are spoken by the patient, the messages cause the system program to alter the operation of the pacemaker. In different embodiments, a message derived from the speech information may cause the system program to alter the operation of the pacemaker by, for example, changing its operating mode, changing the operating parameters such as minimum heart rate, or causing the pacemaker to begin storage of sampled data in a storage medium such as the system memory 12.

Examples of such data storage include samples of the acoustic transducer output which therefore constitute recordings of the patient's voice or heart sounds, and samples of the sensing channel outputs thus forming a cardiac electrogram. Time stamps may also be applied to the recordings as they are made. Other types of data as recorded by other physiologic sensors incorporated into the device could also be recorded. The recordings can be later retrieved by transmission via the telemetry interface to an external programming device. Such recordings of physiological or voice data can then be correlated with symptoms experienced by the patient. This may be very useful to a treating physician in getting an accurate history of a cardiac event experienced by the patient, especially for those patients who are not able to adequately describe a cardiac event at much later clinical visit.

In another embodiment, voice recording is initiated upon receipt by the device of either an externally derived signal or an internal signal generated by the device itself. Examples of such external signals that could be used by particular embodiments are voice commands sensed and interpreted by the device as described above, operation of a magnetically-actuated reed switch with a magnet placed in proximity to the device (as is done to initiate a programming mode in conventional pacemakers), or manual operation of tactilely actuated switch by a user. In the case of a tactilely actuated switch, the tactile sensor actuating the switch could be, for example, a button placed on the outside of the implanted device which a user could access by pressing on the overlying skin, or a vibration sensor or accelerometer such as acoustic transducer 50 where acoustic signals generated by tactile stimuli applied to the device (e.g., by manually tapping) are interpreted as commands to activate voice recording. In another embodiment, voice recording could be activated when an internal signal is generated by the device when a condition corresponding to the onset of a physiologic or cardiac event is sensed by the device. In other embodiments, such externally and internally generated signals can be used to trigger other types of diagnostic storage including, e.g., recording of time stamps, cardiac electrograms, activity sensor outputs, and heart sound sensors, as well as to affect the operation of the device such as adjusting the pacing rate within predefined limits or turning on or off sensor dependent rate-responsive features.

In order to derive speech information from the acoustic transducer output corresponding to the patient's voice or to produce intelligible voice recordings for later playback, the acoustic transducer output must be sampled at some minimum rate. As both processor overhead and the memory requirements of the system increase with the sample rate, it is desirable to sample near this minimum rate. Although human hearing is capable of detecting audio frequencies up to 20 KHz, only a fraction of that bandwidth is needed to transmit normal speech. Phone lines in the U.S., for example, restrict the bandwidth of transmitted audio signals to below 4 KHz in order to prevent aliasing distortion when the signals are digitized. A level 0 digital signal used for transmitting a single voice channel over phone lines in the U.S., for example, is a pulse code modulated signal consisting of an analog voice signal sampled with 8 bits of quantization at a rate of 8000 samples per second. It has been found that intelligible speech can still result if an audio signal is bandlimited to at least as low as 2 KHz, which implies a minimum sampling rate of 4000 samples per second. At 4000 samples per second, a memory requirement of 80 Kilobytes would be needed for a 20 second recording. This figure can be reduced still further using various data compression techniques.

The implantable medical device as described thus enables a patient to affect the operation of the device with voice commands. In order to prevent inadvertent commands being issued to the device and restrict access to its voice control feature, the system could be programmed to ignore all messages derived from transduced speech unless a specific password is first spoken. Another password could be used to cause further speech to be ignored. Alternatively, the voice control feature could be rendered inactive until a specific input signal is received which could be, for example, operation of a reed switch by a magnetic field similar to the way external programmers typically communicate with pacemakers, or operation of a tactile sensor incorporated into the device.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A medical device for implantation into a patient comprising:
   an acoustic transducer configured for receiving acoustic energy from within the patient's body and generating electrical audio signals in accordance therewith;
   sampling circuitry and an analog-to-digital converter for producing digitized samples of a signal received from the acoustic transducer; and
   circuitry for recording of a plurality of samples of the digitized acoustic signals including voice and heart sounds in a storage medium and the acoustic transducer, the sampling circuitry and the circuitry for recording are adapted for implantation into the patient, wherein the circuitry for recording further includes voice recording activation circuitry.

2. The device of claim 1 wherein the recording circuitry is activated to initiate voice recording by operation of a magnetically actuated reed switch.

3. The device of claim 1 wherein the recording circuitry is activated to initiate voice recording by operation of a tactile switch incorporated into the device.

4. The device of claim 1 wherein the recording circuitry is activated to initiate voice recording by a signal generated by the device when a condition corresponding to the onset of a psychological or cardiac event is sensed by the device.

5. The device of claim 1 wherein the transducer is acoustically coupled to the patient's larynx.

6. The device of claim 1, further comprising:
   circuitry for recording physiological data from the patient; and
   circuitry for correlating the plurality of the digitized acoustic signals and the physiological data.

7. The device of claim 1 further comprising circuitry for recording a time stamp when samples of the digitized acoustic signals are received and recorded.

8. A medical device adapted for implantation into a patient, comprising:
   an acoustic transducer for receiving acoustic energy from within the patient's body and generating electrical audio signals in accordance therewith;
   sampling circuitry and an analog-to-digital converter for producing digitized samples of a signal received from the acoustic transducer;
   speech recognition circuitry adapted for recognizing groups of words from the digitized signal and to derive a message therefrom;
   circuitry for interpreting the message and altering the operation of the device in accordance therewith, including storage of the digitized samples of the transducer signal in a storage medium;
   a sensing channel for sensing electrical activity of the patient's heart in whom the device is implanted;
   circuitry for producing digitized samples of the sensed electrical activity; and
   circuitry for recording of a plurality of the digitized samples of the sensed electrical activity in the storage medium.

9. The device of claim 8 further comprising circuitry for recording a time stamp when a selected message is received.

10. A method for controlling the operation of an implantable medical device comprising:
    receiving acoustic energy within a patient's body and generating electrical audio signals in accordance therewith;
    analyzing the audio signals and deriving a message therefrom;
    interpreting the message and altering the operation of the device in accordance therewith, including causing the implantable medical device to begin storage of sampled data in a storage medium, wherein the sampled data includes the message;
    sensing electrical activity of a patient's heart in whom the device is implanted;
    producing digitized samples of the sensed electrical activity; and
    recording a plurality of the digitized samples of the sensed electrical activity in the storage medium.

11. The method of claim 10 further comprising receiving acoustic energy associated with speech from within the patient's body and extracting speech information from the electrical audio signals.

12. The method of claim 10 wherein the implantable medical device is adapted for implantation into a patient.

13. The method of claim 10 further comprising ignoring all messages received until a message corresponding to a spoken password is received.

14. A medical device adapted for implantation into a patient, comprising:
    an acoustic transducer for receiving acoustic energy associated with speech from within the patient's body and generating electrical audio signals in accordance therewith;
    sampling circuitry and an analog-to-digital converter for producing digitized samples of a signal received from the acoustic transducer wherein the electrical audio signal has a bandwidth frequency of at least 2 KHz;
    speech recognition circuitry for analyzing the digitized signal and deriving a message therefrom;
    speech recognition circuitry for recording of a plurality of samples of the digitized acoustic signals in a storage medium;
    circuitry for interpreting the message and altering the operation of the device in accordance therewith.

15. The device of claim 14 further comprising circuitry for recording a time stamp when the message is received.

16. The device of claim 14 wherein the message interpreting circuitry ignores all messages until a message corresponding to a spoken password is received.

17. The device of claim 6 wherein the circuitry for correlating comprises circuitry for recording a time stamp when the digitized acoustic signals and the physiological data are recorded.

18. A medical device adapted for implantation into a patient, comprising:
- an acoustic transducer for receiving acoustic energy from within the patient's body and generating electrical audio signals in accordance therewith;
- sampling circuitry and an analog-to-digital converter for producing digitized samples of a signal received from the acoustic transducer;
- speech recognition circuitry for analyzing the digitized signal and deriving a message therefrom;
- circuitry for interpreting the message and altering the operation of the device in accordance therewith, including storage of the digitized samples of the transducer signal in a storage medium;
- a sensing channel for sensing electrical activity of the patient's heart in whom the device is implanted;
- circuitry for producing digitized samples of the sensed electrical activity;
- circuitry for recording of a plurality of the digitized samples of the sensed electrical activity in the storage medium; and
- circuitry for recording a time stamp when a selected message is received.

19. The medical device of claim 18, wherein the device further includes telemetry circuitry for transmitting the plurality of digitized samples to an external device.

20. The medical device of claim 18, wherein the device further includes:
- activation circuitry to activate the speech recognition circuitry; and
- a reed switch coupled to the activation circuitry, wherein the speech recognition circuitry is activated in response to a signal received from the reed switch.

* * * * *